United States Patent [19]

Walker

[11] 4,226,790

[45] * Oct. 7, 1980

[54] PROCESS FOR OXIDIZING THALLIUM (I) TO THALLIUM (III)

[75] Inventor: Jerry A. Walker, Oshtemo Township, Kalamazoo County, Mich.

[73] Assignee: The Upjohn Company, Kalamazoo, Mich.

[*] Notice: The portion of the term of this patent subsequent to Jan. 16, 1996, has been disclaimed.

[21] Appl. No.: 933,665

[22] Filed: Aug. 14, 1978

Related U.S. Application Data

[63] Continuation-in-part of Ser. No. 807,032, Jun. 16, 1977, Pat. No. 4,135,051.

[51] Int. Cl.$^2$ ............................................. C07F 5/00
[52] U.S. Cl. ............................................. 260/429 R
[58] Field of Search ................................. 260/429 R

[56] References Cited

U.S. PATENT DOCUMENTS

| | | | |
|---|---|---|---|
| 4,058,542 | 11/1977 | Rizkalla et al. | 260/429 R |
| 4,113,756 | 9/1978 | Johnson | 260/429 R |
| 4,115,419 | 9/1978 | Nagheri et al. | 260/429 R |
| 4,115,420 | 9/1978 | Brill | 260/429 R |
| 4,115,421 | 9/1978 | Brill | 260/429 R |

FOREIGN PATENT DOCUMENTS 74-14416  7/1974  Japan ................................. 260/429 R

*Primary Examiner*—Helen M. S. Sneed
*Attorney, Agent, or Firm*—John T. Reynolds

[57] ABSTRACT

Thallium (I) alkanoate salts are oxidized to thallium (III) salts in a liquid medium with a peroganic carboxylic acid in the presence of a reactive form of manganese or ruthenium.

9 Claims, No Drawings

PROCESS FOR OXIDIZING THALLIUM (I) TO THALLIUM (III)

CROSS-REFERENCE

This is a continuation-in-part of application Ser. No. 807,032, filed June 16, 1977, now U.S. Pat. No. 4,135,051, issued Jan. 16, 1979.

INTRODUCTION

This invention relates to chemical processes for oxidizing monovalent thallium ions to trivalent thallium ions. More particularly, this invention provides an improved process for oxidizing monovalent thallium compounds to trivalent thallium compounds, which trivalent thallium compounds, in solid or liquid solution form, have a variety of uses.

BACKGROUND OF THE INVENTION

Uses for trivalent thallium compounds, i.e., thallic compounds, are well documented in the chemical and patent literature. Their uses as oxidizing agents is described, for example, in Rizkalla, et al, U.S. Pat. No. 4,058,542, which not only summarizes prior uses for trivalent thallium but describes and claims therein the conversion of monovalent thallium compounds to a trivalent thallium compound in a liquid medium with molecular oxygen in the presence of a Group VIII noble metal and in the presence of a heterocyclic tertiary amine as promoter. Such process requires the use of molecular oxygen, high pressures, and heterocyclic amine promoters which, if carried along to subsequent reaction steps, could contaminate or interfere with the production or purity of other more valuable products of the overall process.

Other thallium (I) to thallium (III) oxidation procedures are known. For example, Japanese Kokai 74 30,291 (1974) describes the oxidation of thallous salts with oxygen in the presence of fatty acid salts of alkali or alkaline earth metal salts, and chloride or bromides of the metals in the presence or absence of copper or iron salts.

Japanese Kokai 74 13,104 describes the preparation of olefin oxides by oxidation of $C_3$ to $C_5$-aliphatic olefins, said olefin oxidation being effected by the use of air (or oxygen) oxidized liquids comprising (a) thallous salts, (b) aliphatic acid salts or alkali or alkaline earth metals, (c) halides of alkali or alkaline earth metals and, optionally, (d) halides or aliphatic acid salts of copper or iron. A similar disclosure is found in Netherlands Application 6,505,487 (1965).

Also, Japanese Kokai 74 14,416 (1974) discloses the oxidation of thallous acetate to thallic acetate in about 50 percent yield with manganese dioxide. Thus, 3.9 weight parts of thallous acetate, 1.3 weight parts of manganese dioxide, and 100 ml of acetic acid was boiled for five hours to give 0.066 mole/liter of thallium III ion.

U.S. Pat. No. 3,479,262 (1969) describes the oxidation of thallium (I) to thallium (III) ions using cerium (IV) ions as the oxidizing agent in the presence of a noble metal catalyst. Such thallium (III) ion product is then used to oxidize olefins.

The above-exemplified prior art oxidation procedures all require high reaction temperatures (usually boiling), sometimes high pressures and/or long reaction times. Also, the resulting thallium (III) solutions are usually obtained in an aqueous solution containing strong acids (such as hydrochloric acid) which make such thallium (III) ion solutions of little value for some organic chemical conversion processes such as oxidation of enol ethers or some olefin oxidation uses. The above-referenced thallium (I) acetate to thallium (III) acetate using manganese dioxide (Japanese Kokai 74 14,416) requires long reaction times and vigorous conditions, which, in fact, destroy some of thallium (III) once it forms. Also, the manganese dioxide must be regenerated which is also time consuming and not straightforward. The use of cerium (IV) compounds with a noble metal catalyst to oxidize thallium (I) to thallium (III) is probably effective but such procedure requires the regeneration of the cerium (IV) compound which is not economical to do (such requires the use of electrochemical methods to regenerate cerium (IV) ions).

Also of interest is Belgium Patent No. 855,127 (equivalent to German Offenlegungsschrift No. 27 24,190) which discloses the use of hydroperoxides or molecular oxygen with a noble metal catalyst (e.g., platinum metal) and an amine promoter to oxidize thallium (I) to thallium (III). However, this process with molecular oxygen requires expensive catalysts, extreme conditions of pressure and/or temperature long reaction times, and the like, to obtain relatively low yields (under 65%) of thallium (III) ion products, unless autoclaves or other high-pressure equipment are used. The Belgian and German reference process with hydroperoxides allows good yields to be obtained but again, expensive catalysts and the presence of amine promoters are required as are moderate reaction times (1–19 hours), which limit the utility of these processes for use in a catalytic sense.

There is a need in the catalytic oxidation chemical process art for a process for oxidizing thallium (I) to thallium (III) ions under mild conditions to obtain more quickly essentially quantitative yields using relatively low cost, non-complex equipment, and to produce thallium (III) ions in such form that the thallium (III) ion product can be used more directly in a variety of subsequent oxidation or other chemical operations without contaminating such subsequent products with materials from the thallium (III) reaction mixture.

OBJECT OF THE INVENTION

It is an object of this invention to provide an improved process for converting thallium (I) to thallium (III) under process conditions which make possible high conversions under mild chemical conditions.

It is another object of this invention to provide a process for oxidizing thallium (I) ions to thallium (III) ions involving mild chemical conditions, short reaction times, chemically simple equipment, relatively low temperatures (best at 0° C. to 30° C.) and atmospheric pressure to obtain essentially quantitative conversions of thallium (I) ions to thallium (III) ions without the necessity to remove extraneous heterocyclic amino promoter material, supported catalysts or byproducts.

Other objects, aspects, and advantages of this invention will be apparent to those skilled in the art from the description as follows.

SUMMARY OF THE INVENTION

Briefly, this invention provides an improved process for oxidizing monovalent thallium ions to trivalent thallium ions which comprises reacting a monovalent thallium salt of an organic carboxylic acid having a pKa above 2 in a liquid medium with a perorganic acid having a pKa above 2 in the presence of a reactive form of a metal selected from the group consisting of at least one of manganese or ruthenium, said non-thallium reactive metal being provided in a sufficiently soluble form and in an amount sufficient to promote the oxidation of monovalent thallium ions to the trivalent thallium valence state. As perorganic acids, $C_1$ to $C_{10}$-peroxyalkanoic acid, e.g., peracetic acid, and $C_7$ to $C_{12}$-peroxyaryl-hydrocarbylcarboxylic acids, e.g., peroxybenzoic acid, are preferred. As liquid reaction medium, an aqueous or $C_1$ to $C_4$-alkanolic alkanoic acid solution, e.g., aqueous acetic acid is preferred. It is also preferred that the monovalent and trivalent thallium ions be present as compounds thereof having an anion in common with the liquid reaction medium, e.g., use acetate salts of monovalent and trivalent thallium in a liquid medium containing acetic acid.

DETAILED DESCRIPTION OF THE INVENTION

This monovalent thallium to trivalent thallium process improvement was discovered in connection with studies done to improve conversions of enol ethers to 2-aryl-$C_3$ to $C_6$-alkanoate esters, which are useful as intermediates for the production of 2-aryl-$C_3$ to $C_6$-alkanoic acids, which have a variety of known uses, but this thallium (I) oxidation process need not be limited thereto.

This thallium (I) oxidation process can also be used in conjunction with a variety of known chemical operations, including olefin oxidations, and the like. For example, in some situations, it is possible to conduct the thallium (I) to thallium (III) oxidation in the same reaction vessel in which the thallium (III) is used for other oxidation or chemical conversion purposes. One example of such procedure is described in my parent application Ser. No. 807,032, filed June 16, 1977, wherein the thallium (I) ions are oxidized back to the thallium (III) condition in the same reaction mixture in which the thallium (III) ion substance is used to convert the enol ethers to 2-aryl-$C_3$ to $C_6$-alkanoate esters. Alternatively, the oxidation of the thallium (I) ion species to the thallium (III) valence condition can be conducted in a vessel separated from that in which the thallium (III) ions are to be used.

For use in this invention, the thallium ions are provided in the form of salts thereof with an organic carboxylic acid having a pKa above about 2, preferably above 4, which thallium salt will ionize under the reactant mole ratio, solvent and temperature conditions employed to create an electrophilic thallium ion species in the mixture. It has been found according to this invention that these thallium salts are the best thallium ion sources in a process where trivalent thallium ions are to be regenerated, either in the same reaction vessel in which the trivalent thallium ions are used or in a separate vessel for recycling back to the reaction vessel where the trivalent thallium ions are re-used. Examples of organic acid salts of thallium for this purpose include those of the $C_1$ to $C_{10}$-alkanoic acids and the $C_1$ to $C_{10}$-haloalkanoic acids such as the acetate, propionates, isobutyrate, hexanoate, α-chloroacetate, α-bromoacetate, α-chloropropionate, α-bromopropionate, α-chlorobutyrate, and derivatives thereof such as α-cyclohexaneacetic acid, as well as the thallium $C_7$ to $C_{12}$-aryl-hydrocarbon-carboxylate, such as thallium benzoate, naphthoates, acenaphthenecarboxylate salts, and the like. Thallium acetate salts are preferred for reasons of cost and availability.

When the thallium (I) ion to thallium (III) ion conversion is to take place in an aqueous alkanoic acid solution, the solution should contain enough alkanoic acid (e.g., acetic acid) to prevent precipitation of any substantial amounts of thallium (III) ions in the mixture as the thallium (III) oxide. For this reason, when aqueous alkanoic acid as used as the liquid medium for the oxidation, the liquid mixture should contain at least about 5 percent by volume of the alkanoic acid, preferably at least about 50 percent of the alkanoic acid, relative to the total amount of water and alkanoic acid in the mixture.

The monovalent thallium ions (in their dissolved salt form) are oxidized to the trivalent thallium ion state by providing to the liquid medium containing such monovalent thallium ions (a) a perorganic acid, preferably a percarboxylic acid having a pKa above about 2 in an amount which is at least stoichiometrically equivalent to the monovalent thallium content in the mixture in the presence of (b) a reactive form of a non-thallium metal selected from the group consisting of at least one of manganese and ruthenium, said non-thallium reactive metal form being provided in a sufficiently soluble form to promote oxidation of monovalent thallium ions to the trivalent thallium valence state. Generally, these promoter metal compounds are placed in the thallium ion solution phase. The amount of manganese or ruthenium metal or compound thereof needed to catalyze the thallium oxidation is quite small. While less than 1 percent by weight of the non-thallium reactive metal compound, based on the weight of the thallium salt being treated, promotes the oxidation by the percarboxylic acid, it is preferred that from about 1 percent to about 10 percent by weight, relative to the weight of the thallium salt present of the selected non-thallium metal compound catalyst be used.

Examples of useful forms of these manganese and ruthenium oxidation promoter elements include reactive salt forms thereof including the sulfates, halides, the organic acid salts, such as the salts thereof with $C_1$ to $C_{10}$-alkanoic acids, arylcarboxylic acids, such as benzoic acid, and the like, the oxides and hydroxides of such metals as sodium, potassium, lithium and other forms of permanganate ion, as well as organic/inorganic reactive forms of such metals, such as tris (triphenylphosphine) ruthenium dichloride, or dibromide, and the like.

I have found that of these metal promoter compounds, all of them work in a $C_1$ to $C_{10}$-alkanoic acid or aqueous alkanoic acid, e.g., aqueous acetic acid, which contains enough alkanoic acid to prevent hydrolysis of thallium (III) alkanoate in the mixture to thallium (III) oxide, $Tl_2O_3$. Manganese compounds can also be used in organic liquid/aqueous systems such as $C_5$ to $C_{10}$-hydrocarbons free of aliphatic unsaturation or methanol or other liquid alcoholic solvents, or alcohol/water solvent mixtures, including primary, secondary or tertiary alcohols and mixtures of these alcoholic solvents with water. Of the organic liquid media, the ruthenium compounds also work in tertiary alkanols but not so well in primary or secondary alcohol systems. Ruthenium compounds work best in $C_1$ to $C_{10}$-alkanoic acids or aqueous $C_1$ to $C_{10}$-alkanoic acids.

Manganese is the preferred thallium oxidation promoter catalyst. A preferred form of the manganese catalyst is divalent manganese acetate, which is usually available as its tetrahydrate, although other forms of manganese may be used, including manganese $C_1$ to $C_5$-alkanoate salts other than manganese diacetate referred to above, manganese sulfate, manganese chloride or bromide, manganese dioxide, alkali metal permanganates, principally sodium, potassium and lithium permanganates, and the like.

The amount of perorganic acid used is generally approximately stoichiometrically equivalent to the amount of thallium ion in the mixture. However, with a manganese compound as catalyst, the amount of perorganic acid used is not critical since any excess peracid is rapidly decomposed to give a per acid-free solution of trivalent thallium alkanoate salt.

These trivalent thallium ion solutions produced by the oxidation of monovalent thallium ion compounds according to this invention give the same product mixtures in use as are obtained from commercially available trivalent thallium salts under similar conditions. However, I have found according to this invention that the use of percarboxylic acids, such as peracetic acid, to oxidize regenerate or oxidize thallium (I) to thallium (III) offers additional advantages. In some cases, the organic products, such as 2-aryl-$C_3$ to $C_5$-alkanoate esters, and the like, produced using the trivalent thallium ions in the mixture, are stable to the presence of peracid therein. In fact, as indicated above, and as illustrated in the examples hereinbelow, the oxidation of monovalent thallium acetate to trivalent thallium acetate with peracid could be carried out in the presence of the 2-aryl-$C_3$ to $C_5$-alkanoate ester product with little to no apparent effect on the ester of the thallium (I) to thallium (III) reaction. Thus, a sequential addition of peracid oxidant and enol ether or olefin reactant to a single reaction mixture, such that the peracid and organic enol ether or olefin are never present in solution simultaneously allows in situ regeneration of trivalent thallium ions and avoids peracid oxidation of the enol ether or olefin.

Our studies have shown that peracetic acid solutions prepared using a sulfonic acid resin catalyst (as opposed to a soluble acid catalyst such as p-toluenesulfonic acid) are preferred if a large number of cycles of the process is to be carried out. The gradual build-up of strong acid, such as sulfuric acid, which is present in most commercial grades of 40 percent peracetic acid solutions or p-toluenesulfonic acid, if such acids are used as a catalyst in peracid formation, was found to inhibit the thallium (I) to thallium (III) oxidation reaction after a number of cycles. With sulfuric acid-free or sulfonic acid-free peracid solutions, the enol ether plus trivalent thallium ion→ester product and thallium (I) to thallium (III) oxidation reactions proceed readily even after a large number of cycles.

However, commercially available peracetic acid solution, prepared using sulfuric acid in the production, can be used in the process of this invention if a limited number of cycles of the thallium (I) to thallium (III) ion regeneration process are contemplated. If extensive numbers of cycles of use of the thallium ions are intended, it is preferred to use a perorganic acid which is free of strong acid, e.g., free of sulfuric acid, or organic sulfonic acids, used to make perorganic acids for some uses. The preferred perorganic acids for use in the process of this invention can be generated using ion exchange resins containing acid groups by known methods [see Bulletin No. 69 (1958), "Epoxidation and hydroxylation with Becco Hydrogen Peroxide and Peracetic acid", Becco Chemical Division of FMC] and which ion exchange resins can be removed from the perorganic acid by filtration or other physical methods, prior to use in the process of this invention.

In one mode of conducting the process of this invention, the trivalent thallium ions are regenerated from monovalent thallium ions in the reaction mixture, e.g., in the oxidation of an enol ether with structure (I), by providing the peracid to the monovalent thallium ion containing substrate, e.g., enol ether deficient mixture in the presence of a reactive form of manganese or ruthenium. In another mode of the process, the liquid phase containing all or most of the thallium ion content is separated from the liquid phase containing all or most of the substrate, e.g., the products, e.g., the ester materials, and the aqueous thallium ion phase is treated with an effective amount of a perorganic acid as described above in the presence of one or more of the oxidation promoter metals to oxidize the monovalent thallium ions to the trivalent thallium valence state and then the resulting liquid phase containing the trivalent thallium ion rich phase is returned for admixture with the liquid phase containing the substrate, e.g., the enol ether, for conversion thereof to the respective product, e.g., the ester III.

To produce larger quantities of the 2-aryl-$C_3$ to $C_6$-alkanoate esters in the same reaction vessel or in a continuous manner when thallium salts derived from organic acid having a pKa of 2 or higher are used, I have discovered that after essential exhaustion of the first or prior quantities of enol ether in the mixture the trivalent thallium ions needed for further reaction with enol ether can be generated from monovalent thallium ions either contained in that reaction mixture or in a separate vessel by providing or otherwise mixing with the monovalent thallium ion containing mixture at least about a stoichiometric amount, preferably a slight excess, of a peracid derived from an organic carboxylic acid having a pKa about 2 or above in the presence of a reactive form of, preferably salt, oxide or base form of a metal selected from the group consisting of at least one of manganese and ruthenium, said non-thallium metal, salt, oxide or base being provided in a form and concentration, either in the reaction medium or the separate reaction vessel to promote oxidation of monovalent thallium ions to the trivalent thallium valence state. Thereafter the regenerated trivalent thallium ion can be recombined with enol ether, either by adding additional enol ether to the same reaction vessel or by moving and adding the regenerated trivalent thallium ion mixture to the reaction vessel which contains more enol ether with which to react to form the additional 2-aryl-$C_3$ to $C_6$-alkanoate ester. This in situ generation or regeneration of thallium (III) ions from thallium (I) ions allows thallium (III) organic acid salts to be used in an essentially catalytic manner. The utility of these highly toxic, thallium compounds is, thus, greatly extended and the hazards of working with them are greatly reduced. Peracetic acid, which is free of strong acids such as sulfuric acid, is preferred for use in this process. Commercial 40% peracetic acid contains about 1% sulfuric acid.

When the enol ether to ester product reaction is completed or has proceeded to the optimum degree, the ester mixture can be separated from the thallium ion liquid phase, allowed to stabilize to room temperature, and the ester intermediate product recovered from the reaction mixture by conventional procedures. For example, water and a water-immiscible organic solvent can be added. The organic and aqueous phases can be separated and the organic phase containing the ester product can be dried by conventional means, e.g., over sodium sulfate. Removal of the organic solvent from the product ester can be accomplished by vacuum distillation of the solvent which leaves the ester as a residue, which can be further purified by conventional means or the residue can be treated directly to convert the ester to the corresponding 2-aryl-$C_3$ to $C_6$-alkanoic acid product.

In a two-phase system, the organic layer is isolated, washed with water, and concentrated to leave as residue the crude ester product. The aqueous phase containing the thallic salt is then recycled.

The ester intermediate product can be hydrolyzed or otherwise converted to the corresponding acid by conventional means. For example, the ester can be heated with reflux with a mixed aqueous/alcoholic solution of alkali metal hydroxide until the acid is formed, say for 0.5 to 3 hours. On cooling, the reaction mixture can be treated to recover the acid product, e.g., by washing the hydrolyzed reaction mixture with water, extracting with hexane or commercial mixtures of hexanes (e.g., Skellysolve®B), to remove organic solubles, and the aqueous phase acidified and extracted with hexane. The extracts containing the acid product can be washed with aqueous salt solutions and dried. Thereafter, removal of the solvent by vacuum distillation leaves a crystalline acid product or an oil which crystallizes upon standing.

Preferred embodiments for the use of the process of this invention include the preparation of any of the included ester products using thallium salts of a $C_1$ to $C_{10}$-alkanoic acid, preferably of acetic acid, in an organic liquid mixture containing aqueous alkanoic acid to effect enol ether conversion to the ester products. I have discovered that when these thallium alkanoate salts are used in such a common ion alkanoic acid solvent, the non-thallium reactive metal compounds, particularly those of manganese and ruthenium, readily promote the re-oxidation of monovalent thallium ions to the trivalent thallium state. The manganese and ruthenium can also be provided as the acetate or other alkanoate salt thereof. Peracetic acid is the preferred oxidizing acid for use with the acetate salts of the metals in aqueous acetic acid solutions thereof. The process can preferably include the use of a two-phase liquid system comprising aqueous $C_1$ to $C_{10}$-alkanoic acid as one phase to contain the bulk of the thallium and non-thallium oxidation promoter metal compounds, e.g., manganese or ruthenium acetates, and a $C_5$ to $C_{10}$-hydrocarbon free of aliphatic unsaturation as the other liquid phase to contain the bulk of the enol ether reactant and ester product. Examples of such $C_5$ to $C_{10}$-hydrocarbon solvents include pentane, hexane, heptane, octane, decane, benzene, toluene, xylene, norcarane, norpinane, norbornane, and mixtures thereof, including commercial mixtures such as Skellysolve®B, and the like. This process is particularly well adapted for use in combination with processes for preparing $C_1$ to $C_6$-alkyl esters of ibuprofen by reacting a 4-isobutylpropiophenone $C_1$ to $C_6$-alkyl enol ether with trivalent thallium ions in a water-immiscible organic liquid mixture containing an aqueous $C_1$ to $C_{10}$-alkanoic acid, preferably aqueous acetic acid in which the trivalent thallium ions consumed in the enol ether conversion reaction are regenerated in a separated aqueous acid phase by reacting monovalent thallium ions resulting from that reaction with a percarboxylic acid having a pKa above about 2 in an amount at least stoichiometrically equivalent to the monovalent thallium ion content of the mixture in the presence of a reactive form of manganese or ruthenium, said non-thallium reactive metal being provided in a sufficiently aqueous acid soluble form, preferably as their acetate salts, and in amounts to promote or catalyze the oxidation of monovalent thallium ions to the trivalent thallium valence state, for re-use of the trivalent thallium ions to react with additional enol ether reactant.

The invention is further described and exemplified by the detailed preparations and examples which follow, but they are not intended to limit the scope of the invention. The term MeOH means methyl alcohol (methanol), HOAc means acetic acid. TlOAc means thallium acetate, $MnOAc_2$ means manganese diacetate. Temperatures herein are in degrees centigrade. The symbol "~" means "about".

Preparation 1

To a solution of 3.4 gm. (8.92 millimoles) of commercially available thallium triacetate [$Tl(C_2H_3O_2)_3$] in 25 ml. of absolute methanol stirred at room temperature under nitrogen in a 100 ml. round bottom flask, there was added 1.74 gm. (8.53 millimoles) of crude 4'-isobutylpropiophenone methyl ether (enol ether) of the formula

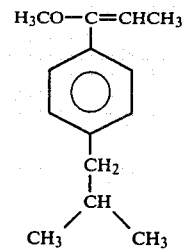

The resulting colorless solution was stirred for twenty-four hours, after which time gas liquid chromatography (glc) analysis of a sample of the reaction mixture indicated that about 95 percent of the enol ether reacted. The resulting reaction mixture was concentrated in vacuo to give a yellow viscous oil which was triturated with hexane and filtered. The resulting hexane solution was washed with aqueous saturated sodium chloride solution and, after separation from the aqueous phase, the hexane solvent was removed in vacuo to give 1.9 gm. of methyl 2-(4-isobutylphenyl)propionate as a pale yellow oil. By glc analysis the oil was about 85 percent pure 2-(4-isobutylphenyl)propionic acid (ibuprofen) methyl ester. NMR analysis of the oil confirmed that the ibuprofen methyl ester was the major product. The crude ester was hydrolyzed as described in the previous example to give 910 mg. of ibuprofen, after recrystallization.

Preparation of Peracetic acid solutions (a) To a stirred solution of 1.1 g (2.7 wt.%) p-toluenesulfonic acid monohydrate in 30 ml glacial acetic acid there was added at room temperature 9.5 ml of 90% hydrogen peroxide; the resulting solution was stirred for about 12–18 hours at room temperature and then stored at 0°–5° C. By iodometric titration the solution consisted of 41% peracetic acid.

(b) To a stirred mixture of 5.0 g (3.1 wt.%) Dowex (MSC-1-H) resin in 120 ml glacial acetic acid there was added 38 ml of 90% hydrogen peroxide. The resulting mixture was stirred at room temperature for 20 hours, then stored at 0° C. By iodometric titration the solution consisted of 41% peracetic acid. Other resins and procedures can be used (see Bulletin No. 69 (1958). "Epoxidation and hydroxylation with Becco Hydrogen Peroxide and Peracetic Acid". Becco Chemical Division of FMC).

EXAMPLE 1

(a) Using Methanol/Acetic Acid Mixture

To a solution of 260 mg. (1.0 mmole) of thallium (I) acetate and about 2 mg. of hydrated manganese diacetate in 4 ml. of methanol and 0.5 ml. of acetic acid there was added, while stirring, 0.4 ml. (2.7 mmole) of 41 percent peracetic acid solution in acetic acid. After thirty minutes of stirring to insure complete reaction to convert thallium (I) to thallium (III) in the mixture, there was added 200 mg. (1.0 mmole) of 4'-isobutylpropiophenone methyl ether (see structure in Preparation I) and the mixture was stirred for 1.5 hours. Gas liquid chromatographic analysis (glc) of a sample of the reaction mixture indicated that about 69 percent of the enol ether had been converted to methyl 2-(4-isobutylphenyl)propionate (ibuprofen methyl ester), based on the starting enol ether. This ester can be used to make ibuprofen therefrom.

(a) Using Aqueous Acetic Acid/Hexane

To a solution of 260 mg. (1.0 mmole) of thallium (I) acetate and 24 mg. (0.1 mmole) of hydrated manganese diacetate in 3 ml. of 80 percent aqueous acetic acid and 4.5 ml. of hexane, there was added 0.3 ml. (about 2.0 mmole) of 42 percent peracetic acid solution in acetic acid. After five minutes of stirring there was added 100 mg. (0.5 mmole) of 4-isobutylpropiophenone methyl enol ether in 0.5 ml. of hexane. After stirring the mixture for about thirty-five minutes, a glc analysis of a sample of the reaction mixture indicated that about 89 percent of the enol ether had been converted to methyl 2-(4-isobutylphenyl)propionate, based on the starting wnol ether.

In the above procedure, manganese diacetate can be replaced by a variety of other manganese salts including manganese (II) 2,4-pentanedionate, manganese (III) 2,4-pentanedionate, manganese triacetate, manganese dioxide, manganese sulate, manganese dichloride and potassium permanganate to obtain oxidation of thallium (I) ions to thallium (III) ions.

EXAMPLE 2

In Situ Regeneration of Thallium (III) Ions

In a 100 ml. 3-necked round bottomed flask with an addition funnel and a reflux condenser there was placed 1.5 g. (5.8 mmole) of thallium (I) acetate, 120 mg. (0.5 mmole) of hydrated manganese diacetate and 15 ml. of acetic acid. The mixture was stirred slowly while 1.5 ml. (10 mmole) of 42 percent peracetic acid in acetic acid solution followed by 25 ml. of hexane was added. The mixture was placed in a 50° C. bath. A 5.0 gm. (2.4 mmole) portion of 4'-isobutylpropiophenone methyl enol ether in about 5 ml. of methanol was placed in the addition funnel. Then one ml. of the enol ether solution, about 500 mg. of the enol ether, was added to the reaction flask from the addition funnel, to form methyl 2-(4-isobutylphenyl)propionate in the mixture.

When the addition of the enol ether was completed and after about three minutes of stirring 0.5 ml. (3.3 mmole) of 42 percent peracetic acid solution was added to effect oxidation of thallium (I) ions in the mixture to the thallium (II) ion state, followed in two minutes by another 1 ml. of enol ether solution to effect formation of more methyl 2-(4-isobutylphenyl)propionate ester in the mixture. This sequential addition of peracetic acid solution and enol ether was continued until addition of the enol ether in the addition funnel was completed. A glc analysis of a sample of the reaction mixture indicated that about 81 percent of methyl (2-(4-isobutylphenyl)-propionate ester (ibuprofen methyl ester) had been formed in this manner, based on the enol ester, from the in situ regenerated thallium (III) ions in the mixture.

The reaction mixture was cooled to room temperature and diluted with about 30 ml. of water. The organic layer was removed and the aqueous layer was extracted with four portions of hexane. The combined hexane extracts were washed with water and concentrated in vacuo to give about 5.0 gm. of a yellow oil. This oil product was dissolved in a mixture of 17 ml. of methanol and 25 ml. of hexane. The resulting solution was treated with 6.5 gm. of 50 percent aqueous sodium hydroxide solution for 1 hour at about 60° C. The mixture was cooled to room temperature, and then 50 ml. of 1 N aqueous sodium hydroxide and 50 ml. of hexane were added and the organic and aqueous layers were allowed to separate. The aqueous layer was acidified with 50 percent aqueous sulfuric acid and then extracted three times with hexane. The hexane extracts were washed with water, dried over sodium sulfate and concentrated in vacuo to give 4.0 gm., about 81 percent weight yield, of 2-(4-isobutylphenyl)propionic acid, now known generically as ibuprofen. Crystallization of the ibuprofen product from hexane gave 3.4 gm., 67 percent yield of ibuprofen. The amount of thallium (I) acetate used was about 23 percent of the stoichiometrically required amount based on the enol ether consumed

EXAMPLE 3

The enol ether to 2-aryl-$C_3$ to $C_\beta$-alkanoate and thallium (I) to thallium (III) ion regeneration process can also be conducted in a continuous manner using a known type of liquid-liquid extraction column reaction apparatus. Thus, for example, such a column can be operated in a counter-current or co-current mode with a solution of thallium (III) acetate in aqueous acetic acid being charged as one stream. A second stream of a solution of 4-isobutylpropipheone methyl enol ether in a water immiscible hydrocarbon such as hexane or heptane is pumped into the column to mix and react with the thallium (III) ion content of the aqueous mixture. The flow of the aqueous acetic acid solution and the hydrocarbon phases are controlled so that phase separation and reaction can take place in the counter-current or co-current column. The temperature of the reaction mixture can be controlled to the desired range, say 0° to 100° C., by the use of heating jackets around the counter-current column or by other equivalent means. The time needed for the conversion of the enol ester to the ester product is quite short, as can be seen from Example 2, so that the reaction contact time or residence time of the liquids in the column can be readily controlled by controlling the flow of the reactant fluids into and out of the column.

The aqueous acetic acid phase rich in thallium (I) ions can be withdrawn from the bottom of the column and piped to a separate vessel where it is contacted with peracetic acid solution in the presence of one of the above-mentioned metal promoter compounds, e.g., manganese acetate, to oxidize the thallium (I) ions in the mixture to the thallium (lll) valence state, and this resulting thallium (lll) rich solution in aqueous acetic acid can be pumped back to the primary counter-current or cocurrent column or Backmix reactor for further reaction with enol ether to form additional quantities of the 2-aryl-$C_3$ to $C_8$-alkanoate ester product.

The hydrocarbon phase containing the 2-aryl-$C_3$ to $C_8$-alkanoate ester product in a counter-current column can be drawn off the top of the column and piped to an appropriate vessel for separation from the hydrocarbon phase, purification and conversion to the corresponding 2-aryl-$C_3$ to $C_8$-alkanoic acid, as described above. The hydrocarbon solvent can be recycled to dissolve more enol ether reactant for reaction in the counter-current column with thallium (lll) ions therein.

Literature descriptions of suitable liquid-liquid counter-current/co-current column extractors can be found, e.g., in E. G. Scheibel, AIChEJ. Vol. 2(1), March 1956; Coulson and Richardson, "Chemical Engineering," pages 748–774, Pergamon Press Ltd., London (1967).

EXAMPLE 4

In a 25 ml. vial was placed 260 mg. (1.0 millimole) of thallium (I) acetate and 4 ml. of glacial acetic acid. With stirring there was added 0.2 ml. of 40% peracetic acid in acetic acid (commercial) followed by a few milligrams of tris(triphenylphosphine)ruthenium dichloride. After 2 hours of stirring this mixture 200 mg. (1.0 mmole) of 4-isobutylpropiophenone methyl enol ether was added neat and the resulting mixture was stirred for 30 minutes. Analysis of the mixture by gas liquid chromatography (glc) methods indicated that about 50% of methyl 2-(4-isobutylphenyl)propionate had been formed based on the starting enol ether.

Similar results were obtained with ruthenium trichloride and ruthenium dioxide. Under the same reaction conditions hafnium tetrachloride, osmium tetroxide, neobium pentachloride, cobalt (ll) 2,4-pentanedionate and cobalt (lll) 2,4-pentanedionate were found to be less effect catalysts for the oxidation of thallium (I) to thallium (lll) acetate but were effective to give methyl 2-(4-isobutylphenyl)propionate in varying amounts.

EXAMPLE 5

Following the procedure of Example 2, the enol ether of the formula

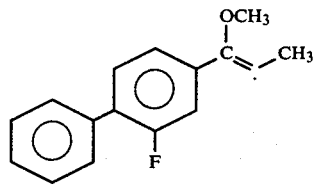

is reacted with thallium (lll) acetate in an aqueous acetic acid/hexane mixture at 25° to 50° C. until methyl 2-(2-fluoro-4-biphenylyl)propionate is formed. This ester is isolated from the reaction mixture and hydrolyzed to 2-(2-fluoro-4-biphenylyl)propionic acid (generic name, flurbiprofen) by the described procedure.

In the same manner, the methyl enol ethers of (a) 6-methoxy-2-naphthyl ethyl ketone, (b) 3-phenoxypropiophenone and (c) p-chloropropiophenone are converted respectively to their corresponding 2-arylpropionate esters, namely to (a) methyl 2-(6-methoxy-2-naphthyl)-propionate [which can be hydrolyzed to the acid 2-(6-methoxy-2-naphthyl)propionic acid, known generically as naproxen]; (b) methyl 2-(3-phenoxyphenyl)propionate [which can be hydrolyzed to the acid 2-(3-phenoxyphenyl)-propionic acid, known generically as fenoprofen]; and (c) methyl 2-(4-chlorophenyl)propionate, which can be hydrolyzed to the acid, 2-(4-chlorophenyl)propionic acid, a known acid.

EXAMPLE 6

Following the procedure of Example 1, the enol ether of isobutyrophenone of the formula

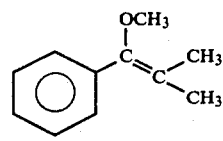

is reacted with thallium (III) acetate to give methyl 2-methyl-2-phenylpropionate. This ester is hydrolyzed to yield 2-methyl-2-phenylpropionic acid.

In a similar manner, the methyl enol ether of 3,4-dichloropropiophenone is converted to methyl 2-(3,4-dichlorophenyl)propionate. This ester is hydrolyzed to the acid, 2-(3,4-dichlorophenyl)propionic acid, which is a known acid having agriculturally significant, weed killing properties.

EXAMPLE 7

Preparation of Ibuprofen via isobutylpropiophenone methyl enol ether starting from p-isobutylbenzene

A. Preparation of p-Isobutylpropiophenone

In a 500 ml. 3-necked, round bottomed flask there was placed 25.50 ml. (40.14 g., 0.29 mmole) of phosphorus trichloride and 43.65 ml. (43.34 g., 0.58 mmole) of propionic acid. This mixture was stirred for 2.25 hours under nitrogen atmosphere at room temperature to prepare the propionyl chloride. By NMR propionyl chloride formation was complete in about 1.5 hours. Then 80 ml. of anhydrous methylene chloride was added and the resulting solution was cooled to about −5° C. (an ice-methanol bath). While stirring the cooled mixture, 87.50 g. (0.66 mmole) of aluminum chloride (technical grade) was added. After 10 minutes of stirring, 67.11 g. (0.50 mmole) of isobutylbenzene was added dropwise from an addition funnel over 55 minutes while maintaining the temperature of the mixture at about 0° to 5° C. The isobutylbenzene was about 99.6% pure and contained about 0.3% n-butylbenzene. The mixture was stirred for an additional 1.25 hours to insure as complete a reaction as possible and then poured into a solution of 250 ml. of ice water and 150 ml. of concentrated hydrochloric acid with vigorous stirring. The Friedal-Crafts reaction was complete in about 45 minutes under these conditions (by GLC analysis). The resulting mixture was extracted three times with 300 ml. portions of methylene chloride. The combined methylene chloride extracts were washed with 250 ml. of water and three times with 250 ml. of molar concentration aqueous sodium carbonate solution. The aqueous sodium carbonate extracts were back-extracted with 100 ml. of methylene chloride and the combined methylene chloride layers were dried over sodium sulfate. The dried methylene chloride solution was concentrated under vacuum to give crude p-isobutylpropiophenone as a pale yellow oil weighing 97.85 g. By GLC analyses, 3% methylene chloride was present. The chemical yield was about 95 g. or about 100% of theory.

B. Preparation of p-isobutylpropiophenone dimethyl ketal

To 11.33 g. (0.10 mole) of methyl acetimidate hydrochloride, prepared by known procedures, in a 100 ml. 3-necked, round-bottomed flask there was added a solution of 9.71 g. (actual 9.42 g.; 49.6 mmole) of crude p-isobutylpropiophenone, prepared as described in Part A above, in 23 ml. of absolute methanol. The resulting solution was stirred for 12 hours at room temperature to insure complete reaction. Gas liquid chromatographic analysis (Glc analysis) of an aliquot of the reaction mixture indicated greater than 99% ketal formation. The resulting mixture was filtered to remove the precipitated ammonium chloride and concentrated under vacuum. Hexane (50 ml.) was added to the residue and the resulting solution was again filtered to remove any acetamide which might be present. Removal of the hexane solvent under vacuum gave p-isobutylpropiophenone dimethyl ketal as a pale yellow oil which was used without further purification. The NMR was in accord.

C. Preparation of 1-(p-isobutylphenyl)-1-methoxy propene (also named p-isobutylpropiophenone methyl enol ether)

In a 100 ml. round-bottomed flask there was placed the crude p-isobutylpropiophenone dimethyl ketal, prepared from 49.6 mmole of crude p-isobutylpropiophenone by the procedure described hereinabove, and 3.0 g. (56.1 mmole) of anhydrous, finely ground ammonium chloride which had been dried under vacuum. Under vacuum (60 mm. Hg.) the mixture was heated with vigorous stirring to 130°–135° C. The pressure was then reduced to 6 to 8 mm. and the mixture was maintained at 130°–135° C. for 3 hours. On cooling, the ammonium chloride was removed by filtration under nitrogen and the solids were washed with 10 ml. of hexane. Concentration of the filtrate under vacuum gave 10.6 g. of a pale yellow oil. By NMR analyses (internal standard nitromethane) the oil consisted of 89.5% of the p-isobutylpropiophenone methyl enol ether and 5% of the p-isobutylpropiophenone dimethyl ketal. It was used without further purification. The overall chemical yield was 9.57 g. (94.6% of theory).

D. Preparation of Ibuprofen via methyl 2-(p-isobutylphenyl)propionate from the p-isobutylpropiophenone methyl enol ether In a 500 ml., 3-necked round-bottomed flask (Morton type) fitted with a mechanical stirrer, a reflux condenser and a thermometer there was placed 39.45 g. (150 mmole) of thallium acetate, 2.8 g. (4.1 mmole) of manganese diacetate.tetrahydrate, 40 ml. of distilled water and 160 ml. of glacial acetic acid. While stirring the resulting mixture there was added about 6 ml. of 41% peracetic acid solution. [The peracetic acid solution was prepared from 60 ml. of glacial acetic acid, 19 ml. of 90% hydrogen peroxide solution and 2.5 g. of a sulfonated polymer resin (Dowex MSC-1-H)]. Once the resulting solution turned dark brown, about 30 to 40 minutes at room temperature, an additional 33 ml. of 41% peracetic acid solution (for a total of about 39 ml., 300 mmole of peracetic acid) was added over about 5 minutes with ice bath cooling. This monovalent thallium oxidation reaction is quite exothermic. The temperature was maintained below 50° C. at all times. The resulting trivalent thallium ion containing solution was placed in an oil bath and the temperature was adjusted to 40° C. With vigorous stirring, a solution of 10.5 g. of crude p-isobutylpropiophenone methyl enol ether, prepared as described above, from 49.7 mmole of crude p-isobutylpropiophenone in 50 ml. of hexane was added via the addition funnel as rapidly as possible. The oxidative rearrangement of the enol ether reaction is exothermic. A 5° C. temperature rise was noted. A glc analysis of an aliquot sample of the reaction mixture after 3 minutes indicated reaction was complete. In other similar runs the reaction time was found to be less than 30 seconds under these conditions. After 17 minutes stirring was discontinued and the mixture was rapidly cooled to 10° C. Upon transfer to a separatory funnel, the hexane layer was removed and the aqueous acetic acid layer was extracted three times with 100 ml. portions of hexane. Hexane extracted essentially all of the desired products (enol ether reactant and ibuprofen ester) from the 80% acetic acid in water acid layer. Dilution of the aqueous acid layer followed by extraction with hexane gave only 160 mg. of additional material which consisted of polar oxidation products such as α-hydroxy-p-isobutylpropiophenone. The combined hexane extracts were washed with three 100-ml. portions of distilled water, 50 ml. of saturated sodium bicarbonate solution, and 50 ml. of saturated sodium sulfate solution. After drying the hexane fraction over sodium sulfate, the dried hexane fraction was concentrated under vacuum to 10.28 g. of crude methyl ibuprofen ester product as a pale yellow oil. By NMR (internal standard-nitromethane) this pale yellow oil contained 90.2% of methyl ibuprofen ester and about 8% p-isobutylpropiophenone, for an overall yield of 9.27 g. (86.6% of theory).

E. Preparation of Ibuprofen from the ester

A 5.11 g. portion of the crude ibuprofen methyl ester prepared as described above was dissolved in 20 ml. of hexane and 12 ml. of methanol and cooled to 0° to 5° C. Then 6.0 g. (75 mmole) of a 50% sodium hydroxide solution was added and the resulting mixture was heated under reflux for 2 hours. On cooling, the mixture was transferred to a separatory funnel with about 50 ml. of 1 N sodium hydroxide solution and hexane. The hexane layer was extracted with about 10 ml. of 1 N aqueous sodium hydroxide and the combined aqueous layer was extracted with 50 ml. of fresh hexane. The neutral fraction isolated from the combined hexane extracts consisted primarily of p-isobutylpropiophenone. The aqueous layer was acidified with 50% aqueous sulfuric acid and extracted 3 times with 50 ml. portions of hexane. The combined hexane extracts were washed 3 times with 50 ml. portions of water and dried over sodium sulfate. Removal of solvent by vacuum evaporation gave crude ibuprofen as a pale yellow solid, weighing 4.20 g., having a purity of 96.7% by Glc analysis, again the impurities being about 1.4% p- isobutylbenzoic acid and 1.1% of the meta isomer of ibuprofen. The crude yield was 80.8% of theory. Recrystallization of the crude ibuprofen from hexane (2 ml./g.) gave 3.44 g. (70.3% chemical yield) ibuprofen.

EXAMPLE 8

Conducting Process in Continuous Manner Using a Scheibel Column

This example demonstrates a series of continuous runs of the process involving reaction between the enol ether (I) (4-isobutylpropiophenone methyl ether), in hexane and trivalent thallium acetate and manganese acetate in an acetic acid-water phase in a continuous apparatus system including a Scheibel column with auxiliary equipment, e.g., pumps, containers, purge tanks, and the like. Scheibel columns are well known in the chemical engineering field. See, e.g., Bulletin No. 33 (1963) of the York Process Equipment Company, 42 Intervale Road, Parsippany, New Jersey, 07054; and "Semicommercial Multistate Extraction Column, Performance Characteristics" by Edward G. Scheibel et al. in *Industrial and Engineering Chemistry*, Vol. 42, No. 6, pp. 1048 et seq.

The two input liquid phase feed compositions were:

(1) an 80% acetic acid in water solution containing 20% w/v trivalent thallium acetate and about 2.7% of divalent manganese diacetate based on the thallium salt content, introduced near the top of the Scheibel column, and (2) hexane containing 20% enol ether reactant introduced near the bottom of the column. The flow rates of the aqueous and hexane phases are adjusted to provide contact in the Scheibel column reactor between the enol ether and thallium ions in a ratio of about 2 molar equivalents of trivalent thallium ions per molar equivalent of enol ether.

The output compositions of the enol ether reactant stream (light phase) are set forth in the table below. A preliminary study of the hydrodynamics (hold up and flood rates) of the system including the Scheibel column was made with pure solvents (blanks) before experimenting with the thallium and enol ether solutions. The experimental conditions were varied from run to run to learn how to maximize the conversion of enol ether to ester product by (1) altering the residence time of the enol ether solution in the column (decreasing or increasing the light phase flow), and/or (2) providing increased mixing efficiency by simultaneously increasing the total throughput in the column and agitator speed (Scheibel, 1956). From the table below it can be seen that the amount of hydrolysis (or by-product ketone formation from the enol ether) is not significant compared to a sequential or batch operation of the process, where usually 5% to 10% of the enol ether reactant is converted to the ketone by-product per batch or sequence. This reduced ketone by-product production in the continuous process is due to the faster reaction rate between the enol ether and the trivalent thallium ions, the low residence time of the enol ether in the Scheibel column reactor part of the system and the relatively slow hydrolysis rate of the enol ether reactant to the undesired ketone by-products.

Since the oxidation of the thallium acetate by peracetic acid is done outside of the main Scheibel column reaction chamber, there are no significant amounts of oxidized by-products, e.g., p-isobutylbenzoic acid.

When the heavier thallium ion/manganese ion acetic acid solution phase drains from the Scheibel column, it contains monovalent thallium acetate, trivalent thallium acetate and manganese diacetate which manganese salt passes through the Scheibel column without reaction. The heavier solution is transferred to a mixing tank where it is reacted with a 40% to 42% peracetic acid solution prepared using p-toluenesulfonic acid or a sulfonated resin bead catalyst for a few minutes (5 to 10 minutes) to effect oxidation of the monovalent thallium ions in the solution mixture in the presence of the manganese acetate catalyst to the trivalent thallium ion state, while by-product oxygen gas is removed from the mixing tank. Thereafter the heavy phase containing the trivalent thallium ions, manganese diacetate in acetic acid/water solution can be concentrated or diluted with acetic acid and water to adjust the concentration of the thallium ions to the desired level before re-introduction of the heavy phase into the Scheibel column reactor for further reaction with enol ether in the lighter hexane phase.

A rough calculation shows that for a 100 kg./day of ibuprofen production a Scheibel column reactor being 0.75 m. long×0.15 m. internal diameter can handle about 100 liters/hour total liquid flow. In this process the degree of mixing in the Scheibel column reactor has been found to be influential in experimental runs to shorten or lengthen residence times.

In these runs (see Table below) the hold-up of the thallium ion phase (heavy phase) in the column is about 75% of the column volume. Applied to the production scale of 100 kg./day of ibuprofen, using the same amount of thallium acetate (required in the enol ether reaction) as indicated above for circulation in the remaining parts of the continuous loop of the apparatus system, the total thallium acetate in the continuous system would be about 5 kg. of thallium acetate, an order of magnitude lower than the amount of thallium ions needed for the sequential operation and about two orders of magnitude lower than that needed for the batch operation.

A sample of the reaction mixture from run number 8 in the table below was worked up to convert the methyl 2-(4-isobutylphenyl)propionate ester product in the mixture to its acid, 2-(4-isobutylphenyl)propionic acid (generic name, ibuprofen). The sample was first washed with 80% acetic acid in water solution and hydrolyzed with sodium hydroxide and then crystallized out of hexane. The total conversion was found to be 63%. However, if correction is made for the unreacted enol ether (since the reaction conditions are not yet optimized and the reaction can be made to go to completion by changing the various parameters available in this system, e.g., flow rate and temperature); the overall conversion of the reacted enol ether is about 92%. This is quite consistent if one scans the column in the Table below showing weight percent of the products in the light liquid phase. The sum of the enol ether (unreacted) and the ibuprofen ester product is in the range of 92% to 97%. This means that with better optimization, it would be possible to achieve about 95±3 percent conversion of the enol ether to isolated ibuprofen acid as compared to about 80±5 percent conversion in the sequential or batch operation.

TABLE A

SUMMARY OF DATA FROM CONTINUOUS REACTION BETWEEN ENOL ETHER AND THALLIUM (III) ACETATE IN A SCHEIBEL COLUMN TO PRODUCE IBUPROFEN

| Expt No. | Light Phase Flow Rate (ml/min) (Enol Ether in Hexane) | Heavy Phase Flow Rate (ml/min) (Tl in 80% HOAc) | Stirring Rate (RPM) | Wt. % Product (G.C.) (Light Phase Output) | | | % Conversion of Enol Ether to Ibuprofen Methyl Ester (Chemical) Yield | % Enol Ether Converted to Ketone | Isolated Product Ibuprofen Yield (Chemical) | |
|---|---|---|---|---|---|---|---|---|---|---|
| | | | | Enol Ether | Ketone | Ibuprofen Methyl Ester | | | Based on Reacted Enol Ether Only | Based on Total Enol Ether Into Column |
| 1 | 8 | 5.5 | 80 | 78 | 8 | 14 | 13 | <1% | — | — |
| 2 | 8 | 3.4 | 80 | 84 | 6 | 10 | 7 | <1% | — | — |
| 3 | 5.8 | 7.8 | 325 | 80 | 7 | 13 | 11 | <1% | — | — |
| 4 | 5.8 | 13 | 325 | 77 | 8 | 15 | 14 | <1% | — | — |
| 5 | 3.7 | 18 | 425 | 67 | 8 | 24 | 24 | <1% | — | — |
| 6 | 3.7 | 24 | 425 | 52 | 9 | 39 | 42 | <1% | — | — |
| 7 | 3.7 | 24 | 590 | 39 | 8 | 53 | 57 | <1% | — | — |
| 8 | 3.7 | 36 | 590 | 29 | 7 | 64 | 68 | <1% | 92% | 63% |
| 9 | 2.2 | 50 | 590 | 18 | 5 | 77 | 80 | <1% | — | — |

Additional Data
(a) No emulsion problems; extremely good separation.
(b) Feed composition:
% EE 90
% ketone 8
Ketal 1.5
% EE in Hexane phase 20
% Tl (OAc) in 80% HOAc phase 20
(c) Hold up in column at end of expt. No. 9:
Light Phase 85 ml.
Heavy Phase 540 ml.
(d) Temperature in Scheibel column 20°–25°
(e) HOAc is acetic acid
EE is p-isobutylpropiophenone methyl ether
ketone is p-isobutylpropiophenone
Ketal is p-isobutylpropiophenone dimethyl ketal In the same manner, the methyl enol ethers of (a) 6-methoxy-2naphthyl ethyl ketone, (b) 3-phenoxypropiophenone and (c) p-chloropropiophenone are converted respectively to their corresponding 2-arylpropionate esters, namely to (a) methyl 2-(6methoxy-2-naphthyl) propionate [which can be hydrolyzed to the acid 2-(6-methoxy-2-naphthyl) propionic acid, known generically as naproxen]; (b) methyl 2-(3-phenoxyphenyl) propionate [which can be hydrolyzed to the acid 2-(3-phenoxyphenyl)-propionic acid, known generically as fenoprofen]; and (c) methyl 2-(4chorophenyl) propionate, which can be hydrolyzed to the acid, 2-(4-chlorophenyl) propionic acid, a known acid.

In a similar manner, the methyl enol either of 3,4-dichloropropiophenone is converted to methyl 2-(3,4-dichlorophenyl) propionate. This ester is hydrolyzed to the acid, 2-(3,4-dichlorophenyl) propionic acid, which is a known acid having agriculturally significant, weed killing properties.

EXAMPLE 9

To a solution of 260 mg (1.0 mmol) thallium (I) Acetate and 20 mg (0.1 mmol) Mn (OAc)$_2$.4H$_2$O in 4 ml glacial acetic acid was added dropwise 0.25 ml (1.7 mmol) 44% peracetic acid (prepared from 90% H$_2$O$_2$ and HOAc with p-toluenesulfonic acid as catalyst) at 25° C. (The term "Ac" herein means an acetyl group.) A vigorous exothermic reaction occurred as the initially colorless solution turned dark brown. After one minute, a test for Tl (I) ion was negative. [An aliquot of the solution was added to a mixture of 1 ml CCl$_4$ and 1 ml of a 0.3% (w/v) solution of iodine monochloride in 6N aqueous HCl. The presence of Tl (I) ion was indicated by the formation of a purple (I$_2$) CCl$_4$ layer. Concentration of greater than 100 ppm Tl(I) ion is easily detected. Thus, the absence of color formation indicates quantitative conversion of Tl(I) to Tl(III)].

Example 10

To a solution of 260 mg Tl(I)OAc and 2 mg Mn(OAc)$_2$.4H$_2$O in 5 ml CH$_3$OH and 0.5 ml HOAc, stirred at 25° C., was added dropwise 0.3 ml 41% peracetic acid (containing catalytic p-toluenesulfonic acid). After the vigorous exothermic reaction subsided (about 1 minute), a test for Tl(I) ion was negative.

EXAMPLE 11

To a solution of 260 mg Tl(I)OAc and 2 mg Mn(OAc)$_2$. 4H$_2$O in t-butyl alcohol stirred at 25° C. was added 0.3 ml 41% peracetic acid solution (p-toluenesulfonic acid catalyst). A check for the presence of Tl(I) ion after 10 minutes was negative indicating quantitative conversation.

EXAMPLE 12

To a solution of 260 mg Tl(I)OAc and 2 mg Mn(OAc)$_2$.4H$_2$O in 4 ml acetic acid and 1 ml of MeOH was added at about 25° C. 0.3 ml 41% peracetic acid solution (p-TSA catalyst). A check for the presence of Tl(I) ion after 10 minutes was negative indicating quantitative conversion.

Addition of 200 mg p-isobutyl propiophenone methyl enol ether (I) to the above solution (after one hour stirring) indicated, after 30 minutes, approximately a 67% conversion to methyl 2-(p-isobutylphenyl)propionate.

EXAMPLE 13

To a solution 260 mg Tl(I)OAc and 21 mg RuO$_2$.H$_2$O in 4 ml HOAc and 1 ml t-butyl alcohol was added at ~25° C. 0.3 ml 41% peracetic acid solution (p-toluenesulfonic acid catalyst). A check for the presence of Tl(I) ion after 15 minutes was negative indicating the quantitative conversion of Tl(I) to Tl(III)OAc.

EXAMPLE 13a

To a solution of 260 mg Tl(I)OAc in 5 ml HOAc was added 0.3 ml 41% peracetic acid solution (p-toluenesulfonic acid catalyst) and 21 mg RuCl$_3$.3H$_2$O. After 15 minutes stirring at 25°, a check for the presence of Tl(I) ion was negative.

EXAMPLE 14

To a solution of 260 mg Tl(I)OAc in 1 ml HOAc and 4 ml t-butyl alcohol was added ~1mg RuO$_2$.H$_2$O and 0.3 ml 41% peracetic acid solution (p-toluenesulfonic acid catalyst). After 15 minutes stirring at room temperature, a check for the presence of Tl(I) ion was negative indicating quantitative conversion to Tl(OAc)$_3$.

EXAMPLE 15

To a solution of 260 mg Tl(I)OAc and about 2 Mn(OAc)$_2$.4H$_2$O and 0.5 ml HOAc with stirring at 25° C. was added 0.4 ml 41% peracetic acid solution (p-toluenesulfonic acid catalyst). After 30 minutes, 200 mg p-isobutyl propiophenone methyl enol ether was added and the resulting mixture was stirred at 25° C. for 3.5 hours. Gas-liquid chromatographic (GLC) analysis of the products indicated a 71% conversion to methyl 2-(p-isobutylphenyl)propionate.

EXAMPLE 16

Repeating Example 15 except that the thallium (I) acetate was contacted with the 0.4 ml 41% peracetic acid in 4 ml MeOH (containing no HOAc) and then with the p-isobutylpropiophenone methyl enol ether with stirring at 25° C. for 3.5 hours. GLC analysis of the products indicated a 64% conversion to methyl 2-(p-isobutylphenyl)propionate.

EXAMPLE 17

To a solution of 1 mmol commercial Tl(III)(OAc)$_3$.1½H$_2$O in 5 ml glacial HOAc was added 1 mmol p-isobutylprophenone methyl enol ether (I) at ~25° C. with stirring. After 30 minutes, analysis of the reaction products by glc indicated ~50% conversion to methyl 2-(p-isobutylphenyl)-propionate (II) hydrolysis of (I) to p-isobutylpropiophenone accounted for most of the remaining products.

Thus, with one equivalent of pure Tl(III)(OAc)$_3$ under such conditions ~50% conversion to (II) is observed. Using this fact, a number of potential catalysts were examined under similar conditions as follows:

To a solution of 1 mmol Tl(I)OAc in 4 ml glacial HOAc was added 1.5 mmol 40% peracetic acid solution (Becco-commercial) followed by 5-10 mg of the test catalyst. After 2 hours of stirring at ~25° C., 1 mmol of the above enol ether (I) was added. After a 30-minute reaction time at 25° C., the products were analyzed by glc. The results were then compared to those obtained when pure Tl(III)(OAc)$_3$.1½H$_2$O was used. Table 1 indicates the results obtained with a number of test catalysts:

TABLE 1

| Catalyst | % conversion to (II)* observed | | |
|---|---|---|---|
| 10. none | 0 | 1. Mn(acac)$_2$ | ~50 |
| 11. HfCl$_4$ | ~5 | 2. Mn(acac)$_3$ | 50 |
| 12. TiO (acac)$_2$ | 0 | 3. Mn(OAc)$_3$ | 58 |
| 13. Zr(acac)$_4$ | 0 | 4. MnSO$_4$ | 56 |
| 14. V(acac)$_3$ | 0 | 5. MnCl$_2$ | 47 |
| 15. VO(acac)$_2$ | 0 | 6. KMnO$_4$ | 53 |
| 16. NbCl$_5$ | ~5 | 7. MnO$_2$ | 54 |
| 17. Cr(acac)$_3$ | 0 | 8. ($\phi_3$P)$_3$RuCl$_2$** | 50 |
| 18. MoO$_2$(acac)$_2$ | 0 | 9. RuCl$_3$ . H$_2$O | 42 |
| 19. Tungstic acid | 0 | | |
| 20. W(CO)$_6$ | 0 | | |
| 21. ReCl$_5$ | 0 | | |
| 22. Fe(acac)$_3$ | 0 | | |
| 23. OsO$_4$ | ~5 | | |
| 24. Co(acac)$_2$ | ~12 | | |
| 25. Co(acac)$_3$ | ~10 | | |
| 26. ($\phi_3$P)$_3$RhCl$_2$ | 0 | | |
| 27. ($\phi_3$P)$_3$IrCl$_2$ | ~5 | | |
| 28. Ni(acac)$_2$ | 0 | | |
| 29. ($\phi_3$P)$_3$PdCl$_2$ | 0 | | |
| 30. H$_2$PtCl$_6$ . H$_2$O | 0 | | |
| 31. Cu(acac)$_2$ | 0 | | |
| 32. AgOAc | 0 | | |
| 33. HAuCl$_6$ . 3H$_2$O | 0 | | |
| 34. Zn(acac)$_2$ | 0 | | |
| 35. Hg(OAc)$_2$ | 0 | | |
| 36. Al(acac)$_3$ | 0 | | |
| 37. Mg(acac)$_2$ | 0 | | |

*Pure Tl(III)(OAc)$_3$ . 1½ H$_2$O gives ~50-60% conversion
**($\phi_3$P)$_3$RuCl$_2$ = tris(triphenylphosphine)ruthenium chloride
(acac) means "acetylacetonate"

EXAMPLE 18

To a solution of 500 mg Tl(I)OAc and 40 mg of Mn(OAc)$_2$.4H$_2$O in 4 ml HOAc and 1 ml H$_2$O stirred at 25° C. was added 6.5 ml 44% peracetic acid solution [prepared with Dowex (MSC-1-H)resion] dropwise over a few minutes as the mixture turned dark brown and a vigorous exothermic reaction occurred. A check for the presence of thallium (I) ion after a short reaction time was negative indicating the quantitative conversion of Tl(I) to Tl(III) acetate.

EXAMPLE 19

To a solution of 1.0 g Tl(I)OAc and 80 mg of Mn(OAc)$_2$.4H$_2$O in 5 ml (7:3) HOAc-H$_2$O with stirring at ~25° C. was added dropwise 1.0 ml 44% peracetic acid solution [prepared with Dowex (MSC-1-H)resion]. After about 10 minutes, a check for the presence of Tl(I) ion was negative.

EXAMPLE 20

To a solution of 1.0 g Tl(I)OAc and 80 mg of Mn(OAc)$_2$.4H$_2$O in 5 ml (9:1) HOAc-H$_2$O was added dropwise at 25° C. 1.0 ml of 44% peracetic acid solution [prepared with Dowex (MSC-1-H)resion]. After a few minutes, a check for Tl(I) ion was negative.

I claim:

1. A process for oxidizing monovalent thallium ions to trivalent ions which comprises reacting a monovalent thallium salt of an organic carboxylic acid having a pKa above about 2 in a liquid medium with a perorganic acid having a pKa above 2 in the presence of a reactive form of manganese said manganese being provided in a sufficiently soluble form and in an amount sufficient to promote the oxidation of monovalent thallium ions to the trivalent thallium valence state.

2. A process according to claim 1 wherein the monovalent thallium ions are oxidized to the trivalent thallium ion state in a reaction medium wherein the perorganic acid is a C$_1$ to C$_{10}$-peroxyalkanoic acid or a C$_7$ to C$_{12}$-peroxyaryl hydrocarbon-carboxylic acid.

3. A process according to claim 1 wherein the liquid medium for the monovalent thallium ion to trivalent thallium ion oxidation reaction is an aqueous alkanoic acid solution containing at least 5 percent by volume of the alkanoic acid.

4. A process according to claim 3 wherein the monovalent thallium ion and the trivalent thallium ions producted in the oxidation reaction mixture have an alkanoate ion in common with the alkanoic acid in the liquid reaction medium.

5. A process according to claim 4 wherein the monovalent thallium ions are present in the form of thallium acetate salts and the liquid reaction medium is an aqueous solution of acetic acid.

6. A process according to claim 1 wherein the monovalent thallium ions are oxidized to the trivalent thallium valence state in a liquid reaction mixture by reaction with the perorganic acid in the presence of an oxidation promoting amount of a reactive form of manganese.

7. A process according to claim 6 wherein the manganese is selected from the group consisting of manganese $C_1$ to $C_6$-alkanoate salts, manganese sulfate, manganese chloride or bromide, manganese dioxide and on alkali metal permanganate.

8. A process according to claim 5 wherein the perorganic acid used is peracetic acid in the presence of an oxidation promoting amount of manganese (II) diacetate.

9. A process according to claim 6 wherein the reaction medium is aqueous acetic acid and the perorganic acid used is peracetic acid.

* * * * *